(12) United States Patent
Mazor et al.

(10) Patent No.: US 7,653,174 B2
(45) Date of Patent: Jan. 26, 2010

(54) INSPECTION OF SMALL FEATURES USING X-RAY FLUORESCENCE

(75) Inventors: Isaac Mazor, Haifa (IL); David Berman, Kiryar Tivon (IL); Boris Yokhin, Nazareth Illit (IL); Alexander Tokar, Haifa (IL)

(73) Assignee: Jordan Valley Semiconductors Ltd., Migdal Ha'emek (IL)

( * ) Notice: Subject to any disclaimer, the term of this patent is extended or adjusted under 35 U.S.C. 154(b) by 0 days.

(21) Appl. No.: 12/003,215

(22) Filed: Dec. 20, 2007

(65) Prior Publication Data

US 2008/0159475 A1 Jul. 3, 2008

(30) Foreign Application Priority Data

Jan. 1, 2007 (IL) .................................. 180482

(51) Int. Cl.
*G01N 23/223* (2006.01)

(52) U.S. Cl. ........................................ 378/50

(58) Field of Classification Search ........... 378/42, 378/45, 48, 50, 70, 71, 73, 74, 76, 82–86, 378/88, 89
See application file for complete search history.

(56) References Cited

U.S. PATENT DOCUMENTS

| | | | |
|---|---|---|---|
| 3,980,568 A | 9/1976 | Pitchford et al. | |
| 4,446,568 A | 5/1984 | Williams et al. | |
| 4,590,603 A * | 5/1986 | Relihan et al. | 378/108 |
| 4,718,075 A * | 1/1988 | Horn | 378/91 |
| 4,725,963 A | 2/1988 | Taylor et al. | |
| 4,847,882 A | 7/1989 | Knoth et al. | |
| 4,916,720 A | 4/1990 | Yamamoto et al. | |
| 4,989,226 A | 1/1991 | Woodbury et al. | |
| 5,151,588 A | 9/1992 | Kiri et al. | |
| 5,425,066 A * | 6/1995 | Takahashi et al. | 378/50 |
| 5,481,109 A | 1/1996 | Ninomiya et al. | |
| 5,574,284 A | 11/1996 | Farr | |
| 5,619,548 A | 4/1997 | Koppel | |
| 5,740,226 A | 4/1998 | Komiya et al. | |
| 5,900,645 A | 5/1999 | Yamada | |
| 5,909,276 A | 6/1999 | Kinney et al. | |
| 5,923,720 A | 7/1999 | Barton et al. | |
| 5,937,026 A | 8/1999 | Satoh | |
| 5,949,847 A | 9/1999 | Terada et al. | |
| 5,963,329 A | 10/1999 | Conrad et al. | |

(Continued)

OTHER PUBLICATIONS

Dane et al., "Application of Genetic Algorithms for Characterization of Thin Layered Materials by Glancing Incidence X-Ray Reflectometry", Physica B 253 (1998) 254-268.

(Continued)

*Primary Examiner*—Edward J Glick
*Assistant Examiner*—Mona M Sanei
(74) *Attorney, Agent, or Firm*—Smith, Gambrell & Russell, LLP (57) ABSTRACT

A method for inspection includes irradiating a sample using an X-ray beam, which is focused so as to define a spot on a surface of the sample. At least one of the sample and the X-ray beam is shifted so as to scan the spot along a scan path that crosses a feature on the surface. Respective intensities of X-ray fluorescence emitted from the sample responsively to the X-ray beam are measured at a plurality of locations along the scan path, at which the spot has different, respective degrees of overlap with the feature. The intensities measured at the plurality of the locations are processed in order to compute an adjusted value of the emitted X-ray fluorescence over the scan path. A thickness of the feature is estimated based on the adjusted value.

12 Claims, 5 Drawing Sheets

U.S. PATENT DOCUMENTS

| | | |
|---|---|---|
| 6,041,095 A | 3/2000 | Yokhin |
| 6,041,098 A | 3/2000 | Touryanski et al. |
| 6,108,398 A | 8/2000 | Mazor et al. |
| 6,192,103 B1 | 2/2001 | Wormington et al. |
| 6,226,347 B1 | 5/2001 | Golenhofen |
| 6,226,349 B1 | 5/2001 | Schuster et al. |
| 6,351,516 B1 | 2/2002 | Mazor et al. |
| 6,381,303 B1 | 4/2002 | Vu et al. |
| 6,389,102 B2 | 5/2002 | Mazor et al. |
| 6,453,002 B1 | 9/2002 | Mazor et al. |
| 6,453,006 B1 | 9/2002 | Koppel et al. |
| 6,507,634 B1 | 1/2003 | Koppel et al. |
| 6,512,814 B2 | 1/2003 | Yokhin et al. |
| 6,556,652 B1 | 4/2003 | Mazor et al. |
| 6,639,968 B2 | 10/2003 | Yokhin et al. |
| 6,643,354 B2 | 11/2003 | Koppel et al. |
| 6,680,996 B2 | 1/2004 | Yokhin et al. |
| 6,704,661 B1 | 3/2004 | Opsal et al. |
| 6,711,232 B1 | 3/2004 | Janik |
| 6,744,850 B2 | 6/2004 | Fanton et al. |
| 6,744,950 B2 | 6/2004 | Aleksoff |
| 6,750,952 B2 | 6/2004 | Grodnensky et al. |
| 6,754,304 B1 | 6/2004 | Kumakhov |
| 6,754,305 B1 | 6/2004 | Rosencwaig et al. |
| 6,771,735 B2 | 8/2004 | Janik et al. |
| 6,810,105 B2 | 10/2004 | Nasser-Ghodsi et al. |
| 6,823,043 B2 | 11/2004 | Fewster et al. |
| 6,895,075 B2 | 5/2005 | Yokhin et al. |
| 6,947,520 B2 | 9/2005 | Yokhin et al. |
| 6,977,986 B1 | 12/2005 | Beanland et al. |
| 7,023,954 B2 | 4/2006 | Rafaeli et al. |
| 7,062,013 B2 | 6/2006 | Berman et al. |
| 7,068,753 B2 | 6/2006 | Berman et al. |
| 7,071,007 B2 | 7/2006 | Tseng et al. |
| 7,103,142 B1 | 9/2006 | Agnihotry et al. |
| 7,110,491 B2 | 9/2006 | Mazor et al. |
| 7,120,228 B2 | 10/2006 | Yokhin et al. |
| 7,130,376 B2 | 10/2006 | Berman et al. |
| 7,245,695 B2 | 7/2007 | Mazor et al. |
| 2001/0028699 A1 | 10/2001 | Iwasaki |
| 2001/0043668 A1 | 11/2001 | Hayashi et al. |
| 2002/0097837 A1 | 7/2002 | Fanton et al. |
| 2002/0110218 A1 | 8/2002 | Koppel et al. |
| 2003/0012337 A1 | 1/2003 | Fewster et al. |
| 2003/0128809 A1 | 7/2003 | Umezawa et al. |
| 2003/0157559 A1 | 8/2003 | Omote et al. |
| 2004/0052330 A1 | 3/2004 | Koppel et al. |
| 2004/0109531 A1 | 6/2004 | Yokhin et al. |
| 2004/0131151 A1 | 7/2004 | Berman et al. |
| 2004/0156474 A1 | 8/2004 | Yokhin et al. |
| 2004/0218717 A1 | 11/2004 | Koppel et al. |
| 2004/0267490 A1 | 12/2004 | Opsal et al. |
| 2006/0062350 A1 | 3/2006 | Yokhin et al. |
| 2006/0062351 A1 | 3/2006 | Yokhin et al. |
| 2006/0274886 A1* | 12/2006 | Mazor et al. ............ 378/71 |

OTHER PUBLICATIONS

T.C. Huang, "Characterization of Single-and Multiple-Layer Films by X-Ray Reflectometry", Advances in X-Ray Analysis, vol. 35, pp. 137-142, 1992.

Kozaczek, et al., "X-ray Diffraction Metrology for 200 mm Process Qualification and Stability Assessment", Advanced Metallization Conference (Montreal, Canada, Oct. 8-11, 2001.

An English abstract of JP 10 318949, Dec. 4, 1998.

A R Powell, et al., "X-ray diffraction and reflectivity characterization of SiGe superlattice structures", Semicond. Sci. Technol. 7 (1992) 627-631, 1992.

Lengeler, "X-ray reflection, A new tool for investigating layered structures and interfaces", Advances in X-ray Analysis 35 (1992), p. 127.

Lankosz, et al., "Research in quantitative X-ray fluorescence microanalysis of patterned thin films", Advances in X-ray Analysis 43 (1999), pp. 497-503.

Series 5000 Model XTF5011 X-Ray Tube Information, Oxford Instruments Inc., Scotts Valley, GA, U.S.A., Jun. 1998.

J.M. Leng, et al., "Simultaneous measurement of six layers in a silicon on insulator film stack using spectrophotometry and beam profile reflectometry", J. Appl. Physics 81(8), Apr. 1997.

R. Levine Parrill, et al, "GISAXS—Glancing Incidence Small Angle X-ray Scattering", Journal de Physique IV 3 (Dec. 1993), pp. 411-417.

F. Neissendorfer, et al., "The energy-dispersive reflectometer/diffractometer at BESSY-I", Meas. Sci. Technol. 10 (1999), 354-361.

Bowen, et al., "X-Ray metrology by diffraction and reflectivity", Characterization and Metrology for ULSI Technology, 2000 International Conference (American Institute of Physics, 2001).

Ulyanekov, "Introduction to high resolution X-Ray diffraction", Workshop on X-ray characterization of thin layers (Uckley, May 21-23, 2003).

Chihab et al., "New Apparatus for Grazing X-Ray Reflectometry in the Angle-Resolved Dispersive Mode", Journal of Applied Crystallography 22 (1989), p. 460.

Doubly-Bent Focusing Crystal Optic, Produced by XOS Inc., of Albany, New York. Jul. 2000.

An English abstract of JP 09 308339, Dec. 2, 1997.

Model S7032-0908N array, Produced by Hamamatsu, of Hamamatsu City, Japan. May 2000.

U.S. Appl. No. 60/753,895, filed Dec. 22, 2005.

U.S. Appl. No. 60/800,589, filed May 15, 2006.

An English abstract of JP 10 048398, Feb. 20, 1998.

* cited by examiner

INSPECTION OF SMALL FEATURES USING X-RAY FLUORESCENCE

FIELD OF THE INVENTION

The present invention relates generally to non-destructive testing, and particularly to methods and systems for measuring properties of very small features on a substrate.

BACKGROUND OF THE INVENTION

X-ray fluorescence (XRF) measurement, and specifically X-ray microfluorescence (i.e., X-ray fluorescence using narrow, focused excitation beams), is gaining increasing attention as a method for testing semiconductor wafers. XRF itself is a well-known technique for determining the elemental composition of a sample. XRF analyzers generally include an X-ray source, which irradiates the sample, and an X-ray detector, for detecting the X-ray fluorescence emitted by the sample in response to the irradiation. Each element in the sample emits X-ray fluorescence in energy bands that are characteristic of the element. The detected X-ray fluorescence is analyzed to find the energies or, equivalently, the wavelengths of the detected photons, and the qualitative and/or quantitative composition of the sample is determined based on this analysis.

U.S. Pat. No. 6,108,398, for example, whose disclosure is incorporated herein by reference, describes an XRF analyzer and a method for analyzing a sample. The analyzer includes an X-ray beam source, which irradiates a small spot (on the order of 50 μm in diameter) on the sample via a monolithic polycapillary optic. The irradiation causes the sample to emit fluorescent X-ray photons. An array of semiconductor detectors is arranged around the spot so as to capture the fluorescent X-ray photons. The analyzer produces electrical pulses suitable for analysis of the sample.

The use of X-ray microfluorescence for testing semiconductor wafers is described in U.S. Pat. No. 6,351,516, whose disclosure is incorporated herein by reference. This patent describes a non-destructive method for testing the deposition and/or the removal of a material within a recess on the surface of a sample. An excitation beam is directed onto a region of the sample in a vicinity of the recess, and an intensity of X-ray fluorescence emitted from the region is measured. A quantity of the material that is deposited within the recess is determined responsively to the measured intensity.

Another application of X-ray microfluorescence is described by Lankosz et al., in a paper entitled "Research in Quantitative X-ray Fluorescence Microanalysis of Patterned Thin Films," *Advances in X-ray Analysis* 43 (1999), pages 497-503, which is incorporated herein by reference. The authors describe a method for X-ray fluorescence microanalysis using a collimated micro-beam. The method is applied for testing the thickness and uniformity of thin films prepared by ion sputtering techniques.

As yet another example, U.S. Pat. No. 7,245,695, whose disclosure is incorporated herein by reference, describes a method for testing a material applied to a surface of a sample. An excitation beam is directed onto a region of the sample, and the intensity of X-ray fluorescence emitted from the region is measured. The beam may be scanned over a feature on the surface in order to produce a measured XRF profile of the scanned feature. The distribution of the material within the region is estimated based on the measured intensity of the X-ray fluorescence and on the known intensity cross-section of the excitation beam. The method is said to achieve a spatial resolution that is finer than the beam-width of the excitation beam.

SUMMARY OF THE INVENTION

In X-ray-based analysis of fine features on a substrate, such as a semiconductor wafer, it is often difficult to match the beam with sufficient precision to a feature of interest. Precise alignment of the X-ray beam with such a feature may be excessively time-consuming. Furthermore, in some circumstances, even when the X-ray beam is carefully aligned, the overlap between the beam and the feature of interest may be imperfect.

To overcome problems of these sorts, embodiments of the present invention that are described hereinbelow measure the intensity of X-ray emission from a sample at multiple different locations of an irradiating X-ray beam relative to a target feature on the sample. The corresponding intensity measurements are processed in order to give an adjusted value of the emission, which is more accurately indicative of characteristics (such as thickness) of the feature.

Some embodiments of the present invention provide methods and systems for measuring X-ray emission from a feature that is smaller than the diameter of the excitation beam. As a consequence of the small size of the feature relative to the excitation beam, the emitted signal of interest, due to the part of the beam that is incident on the feature, is mixed with background emission from the surrounding region. This problem is particularly marked, for example, in high-energy XRF applications, due to the lack of readily-available X-ray sources and optics for creating narrow X-ray beams at high energies.

Although the embodiments described hereinbelow refer specifically to measurement of XRF from small metal bumps and pads that are formed on the surface of a semiconductor wafer, the principles of the present invention may similarly be applied in XRF measurements on samples of other types, as well as in other areas of radiation emission measurements.

There is therefore provided, in accordance with an embodiment of the present invention, a method for inspection, including:

irradiating a sample using an X-ray beam that includes a central spot having a first diameter and a first incident intensity, and a halo surrounding the central spot and having a second diameter greater than the first diameter and a second incident intensity less than the first incident intensity, in a first irradiation position in which the central spot impinges on a feature on a surface of the sample, the feature having a third diameter, smaller than the second diameter;

measuring a first emitted intensity of X-rays emitted from the sample responsively to the X-ray beam in the first irradiation position;

shifting at least one of the sample and the X-ray beam so that the X-ray beam irradiates the sample in a second irradiation position in which the central spot is displaced off the feature;

measuring a second emitted intensity of the X-rays emitted from the sample responsively to the X-ray beam in the second irradiation position; and comparing the first and second emitted intensities in order to determine a property of the feature.

In some embodiments, measuring the first and second emitted intensities includes measuring X-ray fluorescence emitted from the sample. Typically, measuring the X-ray fluorescence includes measuring the X-ray fluorescence in a selected X-ray emission line that is characteristic of a given element in the sample, and comparing the first and second emitted intensities includes determining a concentration of the given element in the feature. In a disclosed embodiment, the feature includes first and second elements, and measuring the X-ray fluorescence includes measuring the emitted intensities in first and second X-ray emission lines that are respectively characteristic of the first and second elements, and determining the concentration includes computing a ratio of the first and second emitted intensities in order to determine the concentration of the first element in the feature.

In some embodiments, the sample includes a semiconductor wafer, and the feature includes a bump, among multiple bumps that are formed on the surface of the semiconductor wafer, such that the halo irradiates a plurality of the bumps simultaneously. In a disclosed embodiment, shifting the at least one of the sample and the X-ray beam includes displacing one or more of the sample and the X-ray beam so that the central spot impinges on the semiconductor wafer at a location between two of the bumps. Additionally or alternatively, the method includes measuring a height of the bump, wherein comparing the first and second emitted intensities includes using the measured height, together with the intensities, in determining a composition of the bump. Typically, the bumps contain first and second metal elements, and comparing the first and second emitted intensities includes determining a concentration of the first metal element relative to the second metal element.

There is also provided, in accordance with an embodiment of the present invention, apparatus for inspection, including:

an X-ray source, which is configured to irradiate a sample with an X-ray beam that includes a central spot having a first diameter and a first incident intensity, and a halo surrounding the central spot and having a second diameter greater than the first diameter and a second incident intensity less than the first incident intensity;

a motion assembly, which is coupled to move one or more of the X-ray source and the sample so that the X-ray source irradiates the sample in a first irradiation position in which the central spot impinges on a feature on a surface of the sample, the feature having a third diameter, smaller than the second diameter, and in a second irradiation position in which the central spot is displaced off the feature;

a detector assembly, which is configured to measure a first emitted intensity of X-rays emitted from the sample responsively to the X-ray beam in the first irradiation position, and a second emitted intensity of the X-rays emitted from the sample responsively to the X-ray beam in the second irradiation position; and a processor, which is configured to compare the first and second emitted intensities in order to determine a property of the feature.

In a disclosed embodiment, the X-ray source includes an X-ray tube and one or more capillaries, which are configured to receive and focus radiation emitted by the tube.

There is additionally provided, in accordance with an embodiment of the present invention, a method for inspection, including:

irradiating a sample using an X-ray beam, which is focused so as to define a spot on a surface of the sample;

shifting at least one of the sample and the X-ray beam so as to scan the spot along a scan path that crosses a feature on the surface;

measuring respective intensities of X-ray fluorescence emitted from the sample responsively to the X-ray beam at a plurality of locations along the scan path, at which the spot has different, respective degrees of overlap with the feature;

processing the intensities measured at the plurality of the locations in order to compute an adjusted value of the emitted X-ray fluorescence over the scan path; and estimating a thickness of the feature based on the adjusted value.

In a disclosed embodiment, the adjusted value is a maximal value of the emitted X-ray fluorescence over the scan path. Processing the intensity may include fitting a curve to the respective intensities measured as a function of the locations.

In some embodiments, the sample includes a semiconductor wafer on which a scribe line is defined, wherein the feature includes a metal test target formed on the wafer in the scribe line, and wherein shifting the at least one of the sample and the X-ray beam includes scanning the spot across the scribe line. Shifting the at least one of the sample and the X-ray beam may include aligning the X-ray beam with the wafer prior to scanning the spot across the scribe line, and refraining from adjusting an alignment of the X-ray beam relative to the test target while scanning the spot across the scribe line.

In one embodiment, shifting the at least one of the sample and the X-ray beam includes scanning the spot across the feature in a two-dimensional scan pattern. Additionally or alternatively, shifting at least one of the sample and the X-ray beam includes modifying a focal depth of the X-ray beam, and measuring the respective intensities includes determining the respective intensities at two or more different focal depths.

There is further provided, in accordance with an embodiment of the present invention, apparatus for inspection, including:

an X-ray source, which is configured to irradiate a sample with an X-ray beam, which is focused so as to define a spot on a surface of the sample;

a motion assembly, which is coupled to shift at least one of the sample and the X-ray beam so as to scan the spot along a scan path that crosses a feature on the surface;

a detector assembly, which is configured to measure respective intensities of X-ray fluorescence emitted from the sample responsively to the X-ray beam at a plurality of locations along the scan path, at which the spot has different, respective degrees of overlap with the feature; and a processor, which is configured to process the intensities measured at the plurality of the locations in order to compute an adjusted value of the emitted X-ray fluorescence over the scan path, and to estimate a thickness of the feature based on the adjusted value.

The present invention will be more fully understood from the following detailed description of the embodiments thereof, taken together with the drawings in which:

DETAILED DESCRIPTION OF EMBODIMENTS

System Description

Figure 1:
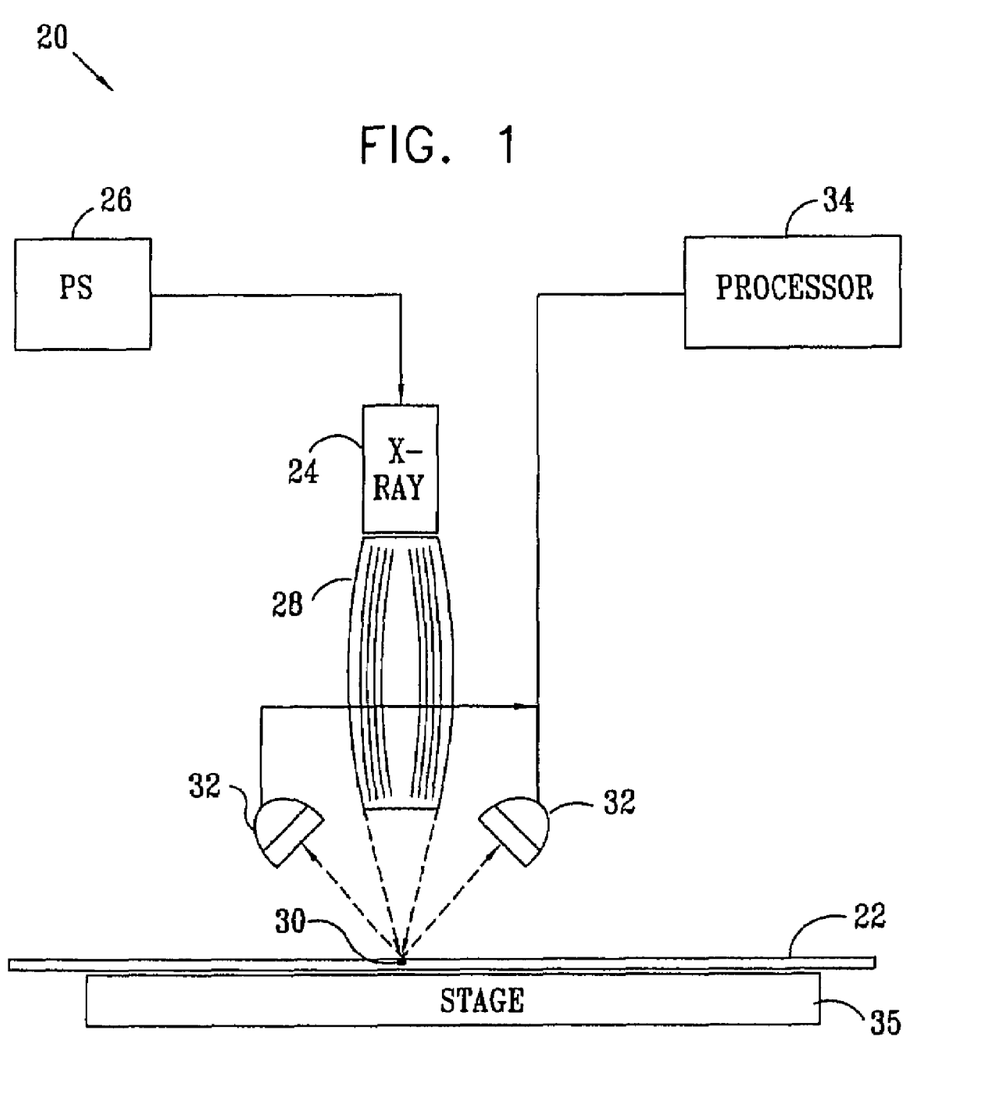
FIG. 1 is a schematic illustration of a system for X-ray microfluorescence measurement, in accordance with an embodiment of the present invention.

FIG. 1 is a schematic illustration of an X-ray microfluorescence analyzer 20, in accordance with an embodiment of the present invention. Aspects of analyzer 20 are described in detail in the above-mentioned U.S. Pat. No. 6,108,398. Analyzer 20 is arranged to examine a sample, such as a semiconductor wafer 22, in order to identify faults in the wafer fabrication process, using methods described hereinbelow.

Analyzer 20 typically comprises an excitation source, such as an X-ray tube 24, driven by a high-voltage power supply 26, as is known in the art. The X-ray tube emits X-rays having a suitable energy range and power flux into X-ray optics 28. The optics may comprise a polycapillary array, for example. Alternatively, a single capillary or other suitable optics may be used, as are known in the art. Optics 28 focus the X-ray beam onto a small region 30 on the surface of sample 22. The irradiated region emits fluorescent X-rays, which are captured by a detector assembly, which typically comprises an array of detectors 32 arranged around region 30 and angled toward it. Responsively to the captured photons, detectors 32 generate electrical signals, which are conveyed to a signal processor 34. The detectors may be of any suitable type, but the inventors have found that for high-energy X-ray measurements, as described hereinbelow, Si(Li) (lithium-drifted silicon) detectors give good results.

Alternatively, other types of fluorescence analyzers known in the art, comprising any suitable excitation source, power source, focusing optics and detection system, may be used for implementing the methods described herein.

Processor 34 typically comprises an energy-dispersive pulse processing system, as is known in the art, which determines an intensity spectrum of the X-ray photons captured by the detectors as a function of photon energy. Alternatively, a wavelength-dispersive detection and processing system may be used. Each chemical element within the irradiated region that is excited by the X-rays from tube 24 emits X-rays in characteristic spectral lines. The intensity of the characteristic spectral lines of a given element is proportional to the mass of that element within region 30. Thus, processor 34 uses the measured intensity spectra to determine properties of the sample or of features on the sample within the area of region 30, particularly the chemical composition of features in the region, i.e., how much of a particular element or elements are present in the region. Processor 34 typically comprises a general-purpose computer, which performs these functions under the control of suitable software. The software may be downloaded to the processor in electronic form, over a network, for example, or it may alternatively be provided on tangible media, such as optical, magnetic or electronic memory media.

As shown in FIG. 1, analyzer 20 is used to examine region 30 on wafer 22. Analyzer 20 comprises a motion assembly for moving either or both of the wafer and the excitation source so that the X-ray beam impinges on the desired point on the wafer surface. In one embodiment, the motion assembly comprises a movable platform, such as an motion stage 35, on which the wafer is mounted so as to enable the wafer to be moved with respect to the X-ray beam. Stage 35 typically performs precise translation of wafer 22 in the wafer (X-Y) plane, and may also adjust the elevation (Z) of the wafer. Alternatively, the wafer may be mounted on a suitable stationary fixture while one or more of the tube 24, optics 28 and detectors 32 are moved, so that the X-ray beam scans the wafer.

Analyzer 20 may be further configured to capture and process X-rays emitted from wafer 22 due to other mechanisms, such as reflection, diffraction, and/or small-angle scattering. Multi-function systems of this sort are described, for example, in U.S. Pat. Nos. 6,381,303 and 6,895,075 and in U.S. Patent Application Publication 2006/0062351, whose disclosures are incorporated herein by reference.

Figure 2:
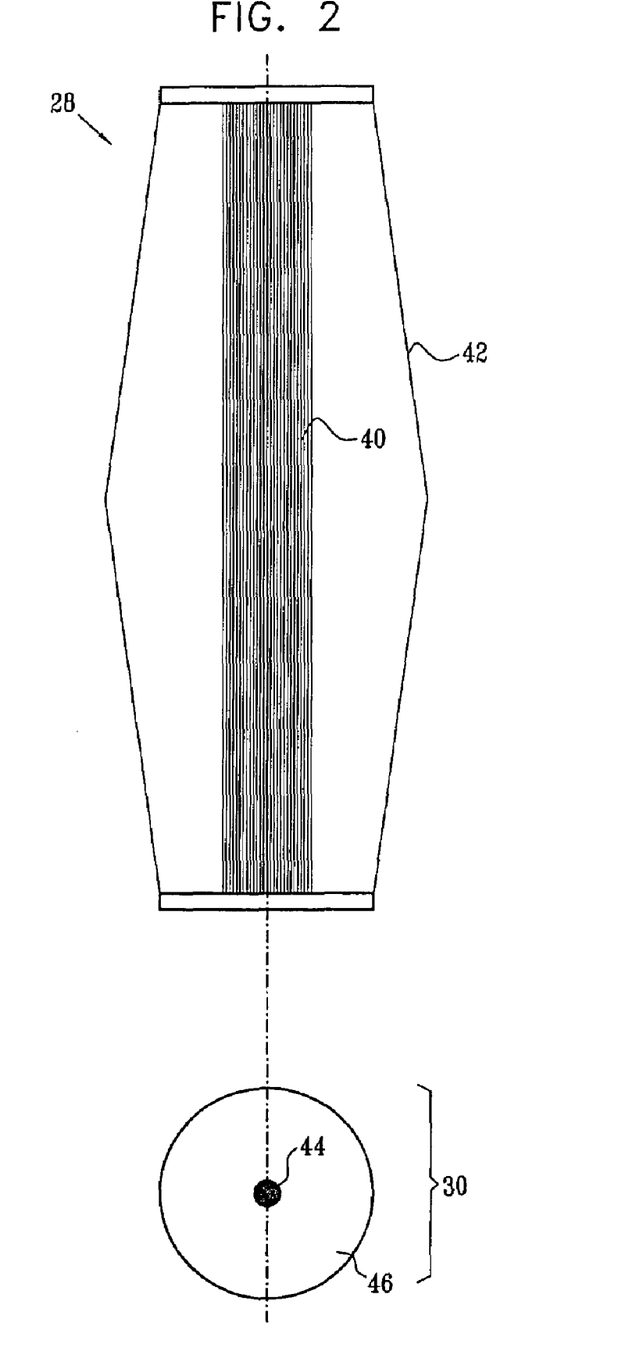
FIG. 2 is a schematic side view of an X-ray polycapillary optic and an X-ray spot formed on a substrate by the optic.

FIG. 2 is a schematic side view of X-ray optics 28 and of region 30. Optics 28 comprise a monolithic polycapillary array 40 in a housing 42. Optics of this sort are available, for example, from X-Ray Optical Systems, Inc. (Albany, N.Y.). In the soft X-ray region, the glass capillaries in array 40 contain and guide the X-rays from tube 24 efficiently, so that the X-rays are focused to a small spot 44, typically about 20 μm in diameter. As X-ray energy increases, at 15-20 keV and above, however, some X-rays escape from the capillaries and create a halo 46, roughly 1 mm in diameter, around spot 44. (Although for simplicity of representation, the boundaries of spot 44 and halo 46 appear to be sharp in FIGS. 2 and 3A, in practice the spot and halo have roughly Gaussian shapes, with blurry boundaries. The approximate diameters cited here refer to the full width at half maximum (FWHM) of the spot and halo.) In experiments in the range of 25-35 keV, for example, the inventors have found that about ⅔ of the X-ray energy transmitted by optics 28 escapes into halo 46. In other words, in the high-energy range, the excitation beam in analyzer 20 comprises central spot 44 of relatively high intensity, surrounded by halo 46 with lower intensity. Both the central spot and the halo give rise to emission of X-ray fluorescence from features on wafer 22 on which they impinge.

Evaluation of Solder Bumps Using High-Energy X-Rays

Figure 3A:
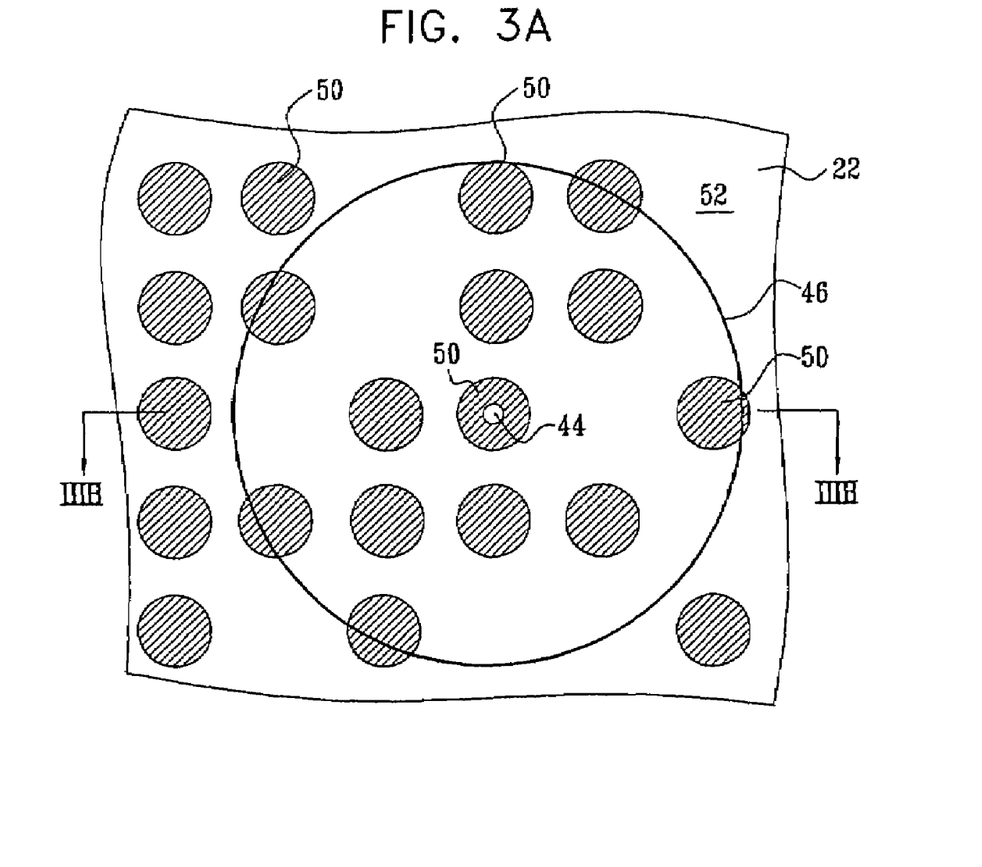
FIG. 3A is a schematic top view of a semiconductor substrate with metal bumps formed thereon, under irradiation by an X-ray beam in accordance with an embodiment of the present invention.
Figure 3B:
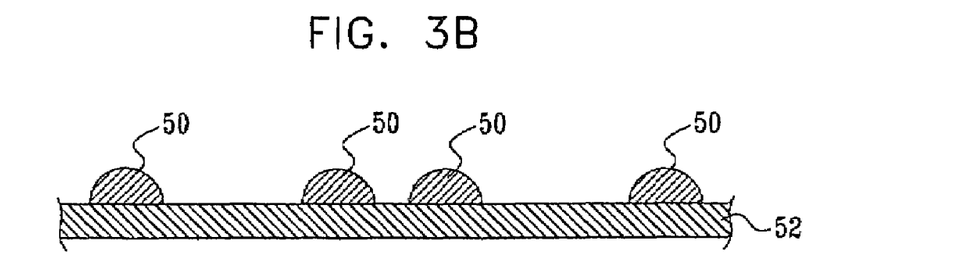
FIG. 3B is a schematic, cross-sectional view of the substrate and bumps shown in FIG. 3A.

FIGS. 3A and 3B schematically show details of an area of wafer 22 that is irradiated by the X-ray beam in analyzer 20, in accordance with an embodiment of the present invention. FIG. 3A is a top view, while FIG. 3B is a cross-sectional view, taken along a line IIIB-IIIB in FIG. 3A. In this example, multiple solder bumps 50 are formed on a substrate 52 on the wafer. Bumps of this sort are commonly used in attaching a semiconductor chip to a circuit substrate (after production of the chip is complete). In a typical manufacturing process, the bumps are about 150 μm in diameter and protrude about 80-100 μm above the surface of substrate 52. For good adhesion and electrical contact with the circuit substrate to which the chip is to be attached, bumps 50 are typically made from tin (Sn) with a few percent of silver (Ag). It is desirable that the percentage of silver in the tin bump be maintained within close limits.

The silver concentration in bumps 50 may be measured in analyzer 20 by comparing the intensity of a characteristic XRF emission line of silver to that of a tin emission line, but a number of problems are encountered in this regard. In the soft X-ray range (such as in the vicinity of the AgLa and SnLa lines, near 3 keV), optics 28 are capable of focusing nearly all of the X-ray energy into spot 44, which is smaller in diameter than bump 50, as shown in FIG. 3A. These energies, however, are strongly absorbed in the metal material of the bumps and thus penetrate less than 10 μm below the bump surface. It has been found experimentally that the distribution of silver within the bumps is not uniform with depth. Therefore, the shallow measurement that can be made using the Lα lines is not accurately representative of the bulk concentration of the silver.

Hard X-rays, such as the AgKα line at 22.1 keV and the SnKα line at 25.2 keV, are capable of penetrating through the entire depth of bumps 50, and thus may be used for accurate bulk measurement of silver concentration. In this case, however, most of the energy in the X-ray beam is spread over halo 46, and only a fraction (about ⅓, as noted above) is concentrated in spot 44. Therefore, a comparison of the AgKα and SnKα XRF intensities in the spot configuration shown in FIG. 3A will not directly give the silver concentration in a single bump, but will rather be a weighted average of the relative concentrations over the entire area of spot 44 and halo 46.

It is possible to use this sort of averaged measurement to estimate the actual average silver concentration in the group of bumps 50 falling within spot 44 and halo 46. For this purpose, the intensity profile of the X-ray beam is calibrated as a function of radial position across spot 44 and halo 46 at the energies of interest. A parametric model of the silver and tin concentrations over the area of the spot and halo is constructed, based on the beam profile and on the actual, known locations of the bumps falling within the area of the halo. (If the measurement is made with region 30 at the same position on multiple, identical dies on a given wafer or multiple wafers of a given type, then the locations of the bumps within spot 44 and halo 46 will be the same for all measurements, and the same model can be used repeatedly.) Processor 34 then fits the parameters of the model to the measured intensities of the AgKα and SnKα emission lines (and/or other lines) in order to find the silver concentration. This approach has the advantage of high throughput, in that it permits the processor to determine average metal concentration over multiple bumps in a single measurement.

Figure 4:
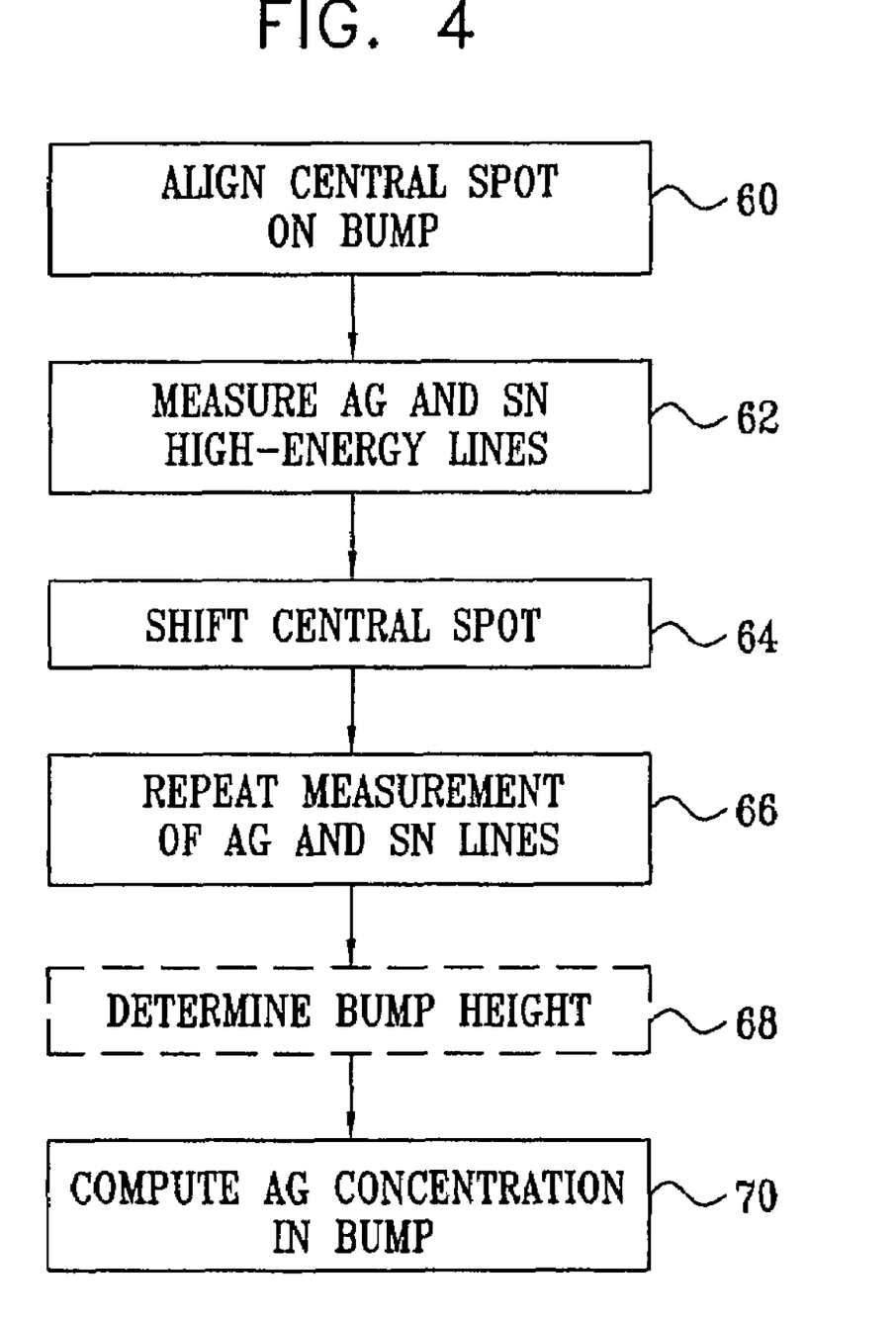
FIG. 4 is a flow chart that schematically illustrates a method for measuring metal concentration in a bump on a substrate, in accordance with an embodiment of the present invention.

FIG. 4 is a flow chart that schematically illustrates a method for measuring silver concentration in a single bump 50, in accordance with an embodiment of the present invention. In this embodiment, processor 34 drives stage 35 so that spot 44 is centered on a particular bump 50 (as shown in FIG. 3A), in an alignment step 60. The processor then actuates X-ray source 24 and detectors 32 to measure the intensity of XRF emission in the AgKα and SnKα lines, at an initial X-ray measurement step 62. Alternatively or additionally, other emission lines may be used, particularly high-energy lines with penetration depths of about 100 μm or greater.

Processor 34 now shifts stage 35 so that spot 44 falls on substrate 52, at a shift step 64. In the example described above and shown in FIGS. 3A and 3B, a shift of about 100-150 μm will move the spot off the central bump onto an area of the substrate between bumps. The aggregate volume of the bumps falling within halo 46, however, will not change significantly. The processor actuates the X-ray source and detectors to repeat the XRF intensity measurement of step 62 at this new position, at a repeat measurement step 66. In the new position, the contribution of halo 46 to the measured XRF emission intensities will be approximately the same as in step 62, but the contribution of spot 44 is negligible. (If desired, steps 64 and 66 may be repeated at two or more different positions, and the measurements averaged in order to determine the halo contribution more accurately.) Thus, the difference between the intensities measured at steps 62 and 66 is roughly equal to the intensity contribution of the portion of bump 50 that was excited by spot 44 at step 62.

The AgKα and SnKα lines have different absorption depths within bumps 50. Therefore, for accurate calculation of the concentration of the silver relative to the tin in a given bump based on the measured intensity of the corresponding XRF lines, it is desirable that the height of the bump above substrate 52 be taken into account. In practice, the inventors have found that the heights of the bumps may vary by roughly ±10 μm. To determine and compensate for these height variations, the height of the bump measured at step 62 may optionally be measured, at a height measurement step 68.

One possibility for this purpose is to measure and compare the intensities of XRF emission at two different lines having different penetration depths, such as the SnLα and SnKα lines. The SnLα emission is absorbed near the surface of the bump, and will therefore be insensitive to bump height. The SnKα emission, on the other hand, penetrates all the way through the bump, and the SnKα intensity will therefore be proportional to the bump height. Comparison of the SnKα and SnLα emission intensities will therefore give a measure of the bump height. Alternatively or additionally, the high voltage on the X-ray tube may be varied over the range of 40-50 keV, giving changes in the observed AgKα/SnKα intensity ratio that can provide another indication of bump height.

Further alternatively, other methods of height measurement may be used at step 68, such as optical triangulation or other methods known in the art.

Processor 34 uses the AgKα and SnKα measurements made at steps 62 and 66 to determine the silver concentration in the bump that was irradiated by spot 44, at a concentration computation step 70. For this purpose, as noted above, the processor subtracts the intensities of the spectral lines measured at step 66 from those measured at step 62 in order to isolate the contribution of spot 44, and thus determine the concentration in the single bump of interest. In converting the intensity ratio between the AgKα and SnKα line to concentration, the processor may take into account the height of the bump measured at step 68. The silver concentration may be derived from the intensity ratio and bump height based on first principles. Alternatively or additionally, the relation between intensity ratio and concentration may be pre-calibrated, using bumps of different, known concentration ratios. This sort of calibration may also be used to take account of (and, if necessary, cancel out the effects of) other elements, such as copper, that may occur in the bumps.

Typically, processor 34 outputs the silver concentration measurement made at step 70 to a user via a suitable output device, such as a monitor connected to processor 34 (not shown). The user compares the measured concentration to the target concentration required by the manufacturing process recipe. If the concentration differs from the target by more than a predefined bound, the user may adjust the process parameters. Alternatively or additionally, analyzer 20 may be integrated with a manufacturing station that is used to produce bumps 50, and processor 34 may automatically give control feedback to the manufacturing station in order to adjust the process parameters as needed.

Measuring Pad Thickness with Imperfect Beam Alignment

The embodiment described above assumes that the spot formed by the X-ray source is aligned accurately with the target feature of interest on the wafer. Such alignment can be achieved, for example, using methods of optical imaging, such as those described in U.S. Pat. No. 6,345,086 or in U.S. Pat. No. 7,023,954, whose disclosures are incorporated herein by reference.

On the other hand, in some applications, accurate alignment of the X-ray spot on the target feature, by optical or other means, is undesirable or infeasible. In the absence of such alignment, however, the X-ray spot may overlap the target feature only partially (or even not at all). This problem can be particularly severe when the diameter of the X-ray spot is of the same order as the width of the target feature. When part of the X-ray spot does not overlap the target feature, a part of the incident X-ray energy is "wasted," and the resulting emission (such as XRF emission) from the feature will be relatively weaker than it would be if the spot were properly aligned with the feature. This weak emission may lead to incorrect estimation of characteristics of the feature, such as its thickness. This problem of imperfect alignment may be overcome by suitable scanning of the X-ray beam over the sample surface and processing of the emitted intensity that is measured at multiple locations along the scan path, as is described in detail hereinbelow.

Figure 5:
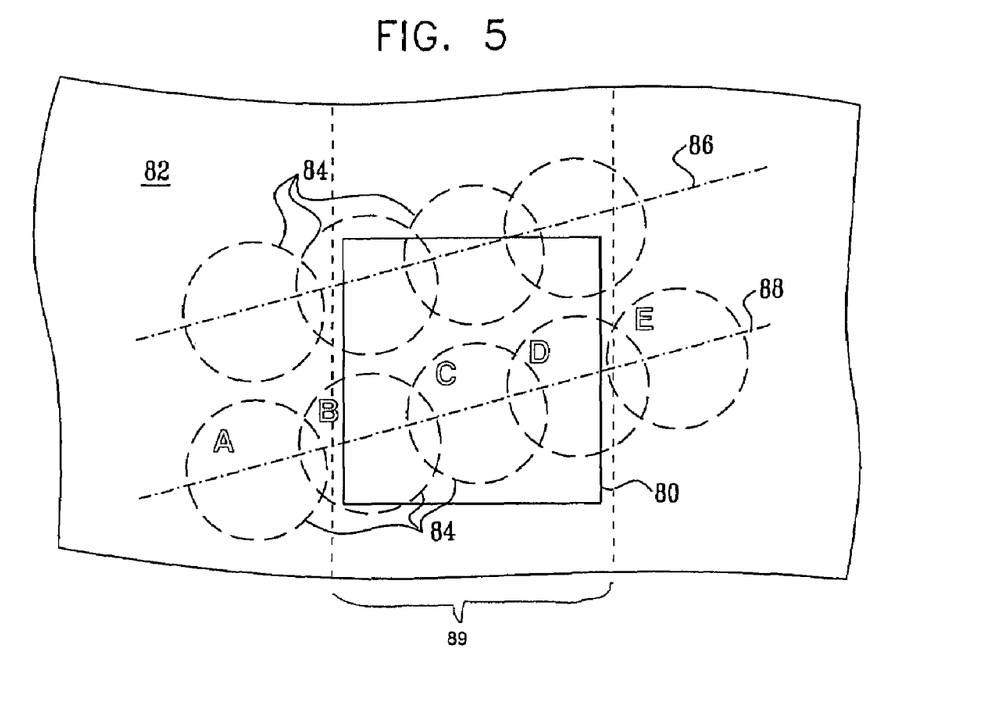
FIG. 5 is a schematic top view of a semiconductor substrate showing scan paths of an X-ray beam over a target feature on the substrate, in accordance with an embodiment of the present invention.

FIG. 5 is a schematic top view of a semiconductor substrate 82 showing scan paths 86, 88 of a spot 84 formed by an X-ray beam on the substrate, in accordance with an embodiment of the present invention. This embodiment, like the preceding embodiment, may be realized using analyzer 20 (FIG. 1) to irradiate and detect XRF emission from substrate 82. Scan paths 86 and 88 cross a target feature, such as a metal pad 80 that is deposited on the substrate. Metal pads of this sort are used, for example, as electrical contact points on a semiconductor wafer, and it is important that the thickness of the metal be within a specified range. The scan may be achieved, as explained above, either by translating the substrate using stage 35 or, alternatively, by shifting the X-ray source, optics and detectors.

In the example shown in FIG. 5, pad 80 is a test pad that is formed in a scribe line 89 on substrate 82. The test pad is formed at the same time and by the same process as the functional contact pads within the dies of the wafer in question, so that the thickness of the test pad gives a good measure of the thickness of the functional pads. In this example, the width of the scribe line is assumed to be approximately 50 µm, while spot 84 has a roughly Gaussian profile with diameter (full width at half maximum—FWHM) of 20-30 µm. These dimensions, however, are given solely by way of illustration, and the principles of this embodiment may be applied over a wide range of dimensions of the X-ray beam and the target feature on which the beam is incident. Furthermore, although pad 80 is shown in FIG. 5 as being approximately square, in practice the pad may be elongated along the scribe line, since the dimensions of features within the scribe line are not constrained by the geometry of the circuits within the adjoining dies. Alternatively, the method described hereinbelow with reference to FIG. 5 may likewise be applied, mutatis mutandis, to functional pads within the die area.

To generate scan paths 86 and 88, substrate 82 is first aligned roughly with the focal point (represented by spot 84) of the beam formed by X-ray source 24 and optics 28. This alignment may be achieved, for example, using optical and/or mechanical alignment on a predetermined fiducial mark. Stage 35 then proceeds to move the substrate so that spot 84 scans across scribe line along path 86, and thereafter along path 88. Typically, the scan stops for a short time at each of a sequence of locations on each scan path, such as the locations marked A, B, C, D, E along path 88. At each location, detectors 32 capture XRF photons emitted from pad 80 and the surrounding area of substrate 82, and the resulting electrical signals generated by the detectors are collected and processed by processor 34. The processor uses the XRF intensities measured at the different locations in order to compute an adjusted value of the emitted X-ray fluorescence over the scan path, as is explained further hereinbelow.

Specifically, processor 34 uses the signals from detectors 32 to count the number of photons emitted in an XRF line that is characteristic of the metal that is used to form pad 80. The number of photons emitted at any given location of spot 84 is proportional to the quantity of metal within the spot, which is in turn proportional to the thickness of the pad and to the area of the pad that is actually overlapped by the spot at the given location. In general, to save time and effort during the scan, stage 35 translates substrate 82 along the scan paths by dead reckoning from the fiducial point that was used for initial alignment, and the alignment of spot 84 with pad 80 is not rechecked or adjusted during the scan. Therefore, it is not possible to know a priori exactly when the spot fully overlaps the pad and whether a low count of XRF photons at a given location of the spot is due to inadequate pad thickness or inadequate overlap between the spot and the pad. In the example shown in FIG. 5, paths 86 and 88 are meant to cross pad 80 in a direction perpendicular to scribe line 89, but the scan axes are misaligned. Therefore, spot 84 overlaps pad 80 completely only at the location marked C on scan path 88, and there may be scans, such as the scan along path 86, in which none of the spot locations provides complete overlap with the pad.

To overcome these difficulties, spot 84 may be scanned in a two-dimensional pattern over the area of pad 80. Thus, for example, scans 86 and 88 may be joined in a raster pattern of parallel scan lines, possibly together with additional parallel scan paths. Alternatively, other two-dimensional scan patterns, such as a spiral pattern, may be used.

As another example, spot 84 may be positioned at each of a matrix of locations, such as a square or rectangular grid of points, possibly a 4×4 grid. By fitting the measurements of XRF intensity at the grid points to an appropriate function, it is possible both to determine the pad thickness and to estimate the positioning error of spot 84 relative to the pad.

As yet another example, the two-dimensional scan may comprise a succession of orthogonal (or otherwise non-parallel) one-dimensional scans. In this case, spot 84 is first scanned along the X-axis, and processor 34 performs a one-dimensional fit, as described hereinbelow, in order to find the maximum value of XRF intensity and the location associated with this maximum. The spot is then scanned along a line in the Y-direction that passes through the location of the maximum found in the X-axis scan. If desired, a new X-direction scan may be carried out along a line that passes through the location of the maximum in the Y-direction scan, and so forth until the maximum value converges or until some other criterion is satisfied, such as a predefined number of scans having been made. The pad thickness may be determined by fitting an appropriate function to all the measurement points.

Further alternatively or additionally, stage 35 may be driven in a two- or three-dimensional scan pattern that includes height variation, in order to vary the focal depth of the X-ray beam on the substrate, and thus vary the size of spot 84. The method of successive orthogonal scans that was described above for the two-dimensional case may be extended to include scanning of the height. At the optimal height of optics 28 above the substrate, the size of the spot on the substrate is minimized, and thus the amount of X-ray beam energy that may be wasted due to spread of the spot over the edge of the pad onto the substrate may also be reduced.

Additionally or alternatively, alignment requirements may be relaxed if pad 80 is elongated along scribe line 89, as mentioned above. In this case, there is a relatively greater likelihood that a roughly-aligned one-dimensional scan across the scribe line will result in good overlap between spot 84 and the pad. Thus, the need for a two-dimensional scan pattern is obviated. Furthermore, even when a one-dimensional scan does not fully overlap the target feature, the computational method that is described below will still enhance the accuracy of the resulting XRF measurement.

Figure 6:
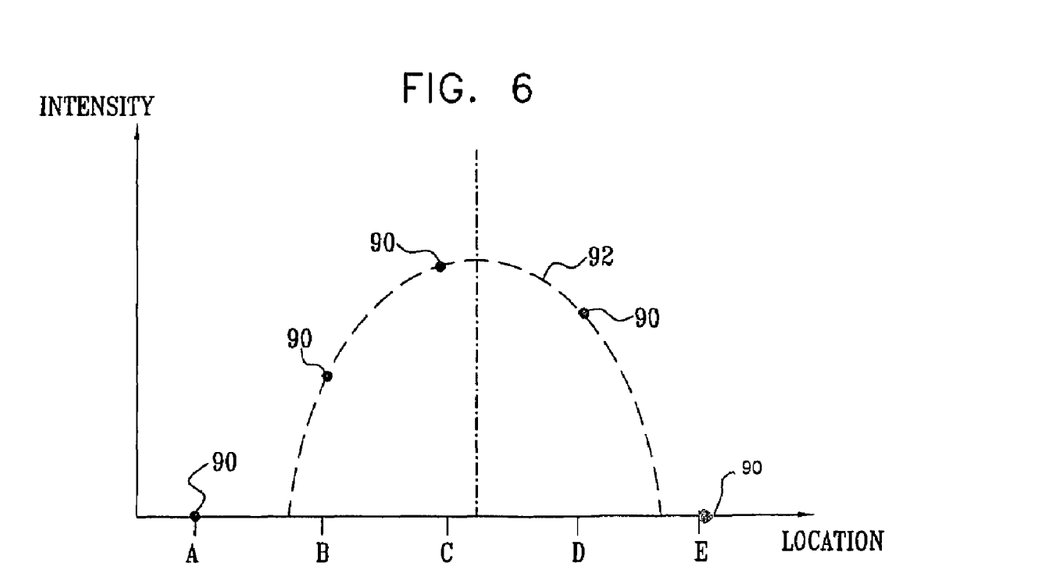
FIG. 6 is a schematic plot of X-ray fluorescence emission intensity from a sample as a function of the location of an X-ray beam irradiating the sample, in accordance with an embodiment of the present invention.

FIG. 6 is a schematic plot of X-ray fluorescence emission intensity from pad 80 on substrate 82 as a function of the location of spot 84 relative to the substrate, in accordance with an embodiment of the present invention. The data in the plot of FIG. 6 are assumed to have been collected during the scan along path 88. Each data point 90 indicates the number of photons counted by processor 34 while spot 84 was incident on the corresponding location (A, B, C, D, E) shown in FIG. 5.

Processor 34 fits a curve 92 through data points 90. Given the roughly circular shape of spot 84 and the straight edges of pad 80, curve 92 is expected to be parabolic. The maximum of curve 92 gives an adjusted value of the emitted X-ray fluorescence from pad 80, which is indicative of the signal that would be received from detectors 32 when the spot is optimally aligned on the pad. For two-dimensional scans, the data may be fitted to a multi-dimensional curve, such as a paraboloid.

Alternatively, the processor may fit any other suitable type of function through the data points or may find the appropriate adjusted value by other methods of computation that are known in the art. For example, the pad thickness T at a given point (X,Y) may be evaluated by integration of the intensity function:

$$T(X, Y) = \alpha \cdot \int_{u=0}^{u=a} \int_{w=0}^{w=b} \mathrm{Spot}(u - X, w - Y) du dw$$

In this equation, the pad is assumed to have dimensions a×b along the X- and Y-axes, respectively, and the X-Y origin is located in the lower left corner of the pad in question. The X-ray spot intensity at a given location $(X_0, Y_0)$ is $I(X,Y)=\mathrm{Spot}(X-X_0, Y-Y_0)$, which can be measured experimentally, as can the constant of proportionality, $\alpha$. A similar function can be measured or calculated for the Z-axis.

Based on this adjusted XRF value, processor 34 estimates the thickness of the metal deposited in pad 80. If the thickness is outside the specified limits, the processor may automatically adjust the process parameters in order to correct the thickness. Alternatively or additionally, the processor may provide an output reading of the thickness, which will enable an operator to monitor the fabrication process and make any necessary adjustments.

CONCLUSION

Although the methods described above are directed to a specific type of measurement (of concentration of certain specific elements in certain types of structure on a semiconductor wafer), the principles of the present invention may be applied generally in XRF measurements of other types of fine features on the surface of a sample, as well as in determining other sample properties using other types of X-ray emission measurements. For example, the methods described hereinabove may be applied, mutatis mutandis, in microanalysis of other heavy elements, such as Ru, Rh, Pd, Cd and In, both in semiconductor manufacturing and in other areas of analysis, such as geology, forensics and archeology.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for inspection, comprising:
    irradiating a sample using an X-ray beam that comprises a central spot having a first diameter and a first incident intensity, and a halo surrounding the central spot and having a second diameter greater than the first diameter and a second incident intensity less than the first incident intensity, in a first irradiation position in which the central spot impinges on a feature on a surface of the sample, the feature having a third diameter, smaller than the second diameter;
    measuring a first emitted intensity of X-rays emitted from the sample responsively to the X-ray beam in the first irradiation position;
    shifting at least one of the sample and the X-ray beam so that the X-ray beam irradiates the sample in a second irradiation position in which the central spot is displaced off the feature;
    measuring a second emitted intensity of X-rays emitted from the sample responsively to the X-ray beam in the second irradiation position; and
    comparing the first and second emitted intensities in order to determine a property of the feature.

2. The method according to claim 1, wherein measuring the first and second emitted intensities comprises measuring X-ray fluorescence emitted from the sample.

3. The method according to claim 2, wherein measuring the X-ray fluorescence comprises measuring the X-ray fluorescence in a selected X-ray emission line that is characteristic of a given element in the sample, and wherein comparing the first and second emitted intensities comprises determining a concentration of the given element in the feature.

4. The method according to claim 3, wherein the feature comprises first and second elements, and wherein measuring the X-ray fluorescence comprises measuring the emitted intensities in first and second X-ray emission lines that are respectively characteristic of the first and second elements, and wherein determining the concentration comprises computing a ratio of the first and second emitted intensities in order to determine the concentration of the first element in the feature.

5. The method according to claim 1, wherein the sample comprises a semiconductor wafer, and wherein the feature comprises a bump, among multiple bumps that are formed on the surface of the semiconductor wafer, such that the halo irradiates a plurality of the bumps simultaneously.

6. The method according to claim 5, wherein shifting the at least one of the sample and the X-ray beam comprises displacing one or more of the sample and the X-ray beam so that the central spot impinges on the semiconductor wafer at a location between two of the bumps.

7. The method according to claim 5, and comprising measuring a height of the bump, wherein comparing the first and second emitted intensities comprises using the measured height, together with the intensities, in determining a composition of the bump.

8. The method according to claim 5, wherein the bumps contain first and second metal elements, and wherein comparing the first and second emitted intensities comprises determining a concentration of the first metal element relative to the second metal element.

9. Apparatus for inspection, comprising:
- an X-ray source, which is configured to irradiate a sample with an X-ray beam that comprises a central spot having a first diameter and a first incident intensity, and a halo surrounding the central spot and having a second diameter greater than the first diameter and a second incident intensity less than the first incident intensity;
- a motion assembly, which is coupled to move one or more of the X-ray source and the sample so that the X-ray source irradiates the sample in a first irradiation position in which the central spot impinges on a feature on a surface of the sample, the feature having a third diameter, smaller than the second diameter, and in a second irradiation position in which the central spot is displaced off the feature;
- a detector assembly, which is configured to measure a first emitted intensity of X-rays emitted from the sample responsively to the X-ray beam in the first irradiation position, and a second emitted intensity of X-rays emitted from the sample responsively to the X-ray beam in the second irradiation position; and
- a processor, which is configured to compare the first and second emitted intensities in order to determine a property of the feature.

10. The apparatus according to claim 9, wherein the detector assembly is configured to measure X-ray fluorescence emitted from the sample responsively to irradiation by the X-ray beam.

11. The apparatus according to claim 9, wherein the sample comprises a semiconductor wafer, and wherein the feature comprises a bump, among multiple bumps that are formed on the surface of the semiconductor wafer, such that the halo irradiates a plurality of the bumps simultaneously.

12. The apparatus according to claim 9, wherein the X-ray source comprises an X-ray tube and one or more capillaries, which are configured to receive and focus radiation emitted by the tube.

* * * * *